(12) United States Patent
Modzelewski et al.

(10) Patent No.: US 9,588,101 B2
(45) Date of Patent: Mar. 7, 2017

(54) APPARATUS FOR DIAGNOSTIC METER STRIP CONTROL AND IDENTIFICATION

(71) Applicant: Trividia Health, Inc., Fort Lauderdale, FL (US)

(72) Inventors: Brent E. Modzelewski, Boca Raton, FL (US); Steven V. Leone, Lake Worth, FL (US); Bradley Combs, Parkland, FL (US)

(73) Assignee: Trividia Health, Inc., Ft. Lauderdale, FL (US)

( * ) Notice: Subject to any disclaimer, the term of this patent is extended or adjusted under 35 U.S.C. 154(b) by 0 days.

(21) Appl. No.: 14/852,030

(22) Filed: Sep. 11, 2015

(65) Prior Publication Data

US 2016/0077039 A1 Mar. 17, 2016

Related U.S. Application Data

(60) Provisional application No. 62/049,710, filed on Sep. 12, 2014.

(51) Int. Cl.
*G01N 27/327* (2006.01)
*G01N 33/487* (2006.01)

(52) U.S. Cl.
CPC ... *G01N 33/48785* (2013.01); *G01N 27/3273* (2013.01)

(58) Field of Classification Search
CPC ..................................... G01N 27/327–27/3274
See application file for complete search history.

(56) References Cited

U.S. PATENT DOCUMENTS

| | | | |
|---|---|---|---|
| 7,166,208 | B2 | 1/2007 | Zweig |
| 7,935,307 | B2 | 5/2011 | Angelides |
| 8,394,328 | B2 | 3/2013 | Neel et al. |
| 8,696,597 | B2 | 4/2014 | Neel et al. |
| 8,702,967 | B2 | 4/2014 | Chinnayelka et al. |
| 8,883,518 | B2 | 11/2014 | Roy et al. |
| 2005/0196820 | A1 | 9/2005 | Zweig |
| 2006/0189895 | A1 | 8/2006 | Neel et al. |
| 2008/0299009 | A1 | 12/2008 | Angelides |

(Continued)

FOREIGN PATENT DOCUMENTS

WO 2007/118046 10/2007

OTHER PUBLICATIONS

PCT International Search Report issued in International Application No. PCT/US2015/049729 mailed Dec. 11, 2015.

*Primary Examiner* — J. Christopher Ball
(74) *Attorney, Agent, or Firm* — Greenberg Traurig, LLP; David J. Dykeman; Roman Fayerberg

(57) ABSTRACT

A system for measuring a property of a sample in a liquid which includes a test strip and a meter is provided. Some embodiments relate to a diagnostic test strip for collecting a sample, the strip having a plurality of electrodes for measuring a property of the sample, and the strip having a control circuit at a distal region of the strip, the control circuit configured to communicate with a controller of a meter, the control circuit including an embedded temperature sensor, a memory for lot coding and authentication of the test strip, and an inhibit logic for inhibiting the test from being used more than once; and a diagnostic meter for receiving the test strip, the meter having a controller programmed to communicate with the control circuit.

23 Claims, 11 Drawing Sheets

(56) References Cited

U.S. PATENT DOCUMENTS

2011/0312004 A1    12/2011   Chinnayelka et al.
2012/0258472 A1    10/2012   Roy et al.
2013/0291626 A1*   11/2013   Sun ..................... A61B 5/145
                                                   73/61.43

* cited by examiner

APPARATUS FOR DIAGNOSTIC METER STRIP CONTROL AND IDENTIFICATION

RELATED APPLICATIONS

This application claims the benefit of and priority to U.S. Provisional Application Ser. No. 62/049,710, filed Sep. 12, 2014, the entirety of which is hereby incorporated herein by reference.

FIELD

The present disclosure relates to electrochemical sensors and, more particularly, to systems and methods for electrochemically sensing a particular constituent within a fluid through the use of diagnostic test strips.

BACKGROUND

Many industries have a commercial need to monitor the concentration of particular constituents in a fluid. In the health care field, individuals with diabetes, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Such systems typically include a test strip where the user applies a blood sample and a meter or meter that "reads" the test strip to determine the glucose level in the blood sample. Because the test strip includes a biological reagent, every strip manufactured is not reproducible with the exact same sensitivity.

It would be advantageous to have a system which would allow for accurate test strip recognition and control.

SUMMARY

The present disclosure is directed to an apparatus for measuring a concentration of an analyte in a body fluid. In some embodiments, the systems of the present disclosure may include a system for measuring a property of a sample analyte with a test strip on which a reaction between the analyte and suitable chemistry can take place, and a meter in electrical communication with the test strip to measure an electrical signal generated by the reaction and to determine the concentration of the analyte.

In some embodiments, the system for measuring a property of a sample in a liquid comprises a diagnostic test strip for collecting a sample, the strip having a plurality of electrodes for measuring a property of the sample, and the strip having a control circuit at a distal region of the strip, configured to communicate with a controller of a meter, the control circuit including an embedded temperature sensor, a memory for lot coding and authentication of the test strip, and an inhibit logic for inhibiting the test from being used more than once; and a diagnostic meter for receiving the test strip, the meter having a controller programmed to communicate with the control circuit. In some embodiments, the control circuit comprises a non-volatile string of bits used to identify the strip as authentic. In some embodiments, the control circuit comprises a non-volatile string of bits used as lot codes. In some embodiments, the controller of the meter is further programmed to perform a test utilizing the test strip, and to subsequently inhibit the test strip from being used again after the test has been completed. In some embodiments, the control circuit is configured to store a glucose value measured during the test. In some embodiments the control circuit is configured to store an error message generated during the test.

In some embodiments, the control circuit is configured to measure other parameters such as a temperature or humidity of the test strip. In some embodiments the control circuit is programmed to inhibit the test strip from being used when the temperature or humidity fall outside of pre-selected ranges of temperature or humidity. In some embodiments, the control circuit is configured to adjust test parameters based on the measured temperature or humidity.

In some embodiments, the system comprises a diagnostic test strip for collecting a sample, the strip having an embedded humidity sensor and a plurality of electrodes for measuring a property of the sample, and the strip having a control circuit at a distal region of the strip, configured to communicate with a controller of a meter, the control circuit including an embedded temperature sensor, a memory for lot coding and authentication of the test strip, and an inhibit logic for inhibiting the test from being used more than once; and a diagnostic meter for receiving the test strip, the meter having a controller programmed to communicate with both the control circuit and the humidity sensor.

In some embodiments, a diagnostic test strip is provided comprising an electrically insulating layer, a conductive pattern formed on the insulating layer including a plurality of electrodes disposed on the insulating layer at a proximal region of the strip, electrical strip contacts disposed on the insulating layer at a distal region of the strip, and conductive traces electrically connecting the electrodes to at least some of the electrical strip contacts, a reagent layer contacting at least a portion of at least one electrode, and a control circuit disposed at the distal region of the strip, connected to the electrodes and configured to communicate with a controller of a meter, the control circuit including an embedded temperature sensor, separate memory for lot coding and authentication, and an inhibit logic. In some embodiments the control circuit comprises a non-volatile string of bits used to identify the strip as authentic. In some embodiments, the control circuit comprises a non-volatile string of bits used as lot codes. In some embodiments, the control circuit is configured to measure a temperature or a humidity of the test strip. In some embodiments the control circuit is programmed to inhibit the test strip from being read when the temperature is outside a pre-selected range of temperatures. In some embodiments, the control circuit may be configured to communicate with the controller to adjust a calculation of a value based on the temperature or humidity measurement. In some embodiments, the control circuit is configured to store a glucose value measured during the test. In some embodiments, the control circuit is configured to store an error message generated during the test. In some embodiments, the test strip further comprises a shell configured to accept the test strip, the shell having a chamber at a distal end, the chamber being configured to accept the test strip and having a first window exposing the electrodes and a second window exposing the contacts to enable connection to the meter to allow for communication with the controller of the meter once the test strip has been inserted into the meter; and a handle at a proximal end of the shell to aid insertion of the test strip into the meter.

In some embodiments, there is provided a method for measuring a concentration of glucose in a blood sample, the method comprising providing a diagnostic test strip for collecting a blood sample, the strip having a plurality of electrodes for measuring a property of the sample, and the strip having a control circuit at a distal region of the strip, configured to communicate with a controller of a meter, the control circuit including an embedded temperature sensor, a memory for lot coding and authentication of the test strip, and an inhibit logic for inhibiting the test from being used more than once; providing a meter for receiving the test strip, the meter having a controller programmed to communicate with the control circuit; inserting the test strip into the meter to enable communication between the controller and the control circuit; causing the control circuit to run diagnostics on the test strip, the diagnostics being one or more of reading autocode information, identifying the test strip, authenticating the test strip, calibrating the analog front end of the test strip, measuring a temperature of the test strip, and validating any electrodes on the test strip; applying a blood sample to the test strip; measuring a resistance of the blood sample and using the resistance to determine the glucose concentration in the blood sample; and causing the controller to inhibit the test strip from being used again.

In some embodiments, the control circuit may include an embedded temperature sensor, an embedded humidity sensor, and separate memories/logic for lot coding, authentication and data storage. In addition, an inhibit logic can be one time programmable (OTP) memory or a digital fuse. These peripherals may be controlled by a controller which interfaces to the meter on the "one wire" interface. In some embodiments, the test strip may contain components, such as thermal fuses, that can operate without the device present, and which can disable the strip in the event that it encounters a temperature or humidity outside the acceptable range. In some embodiments, the humidity sensor may reside outside the control circuit for better environmental exposure.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

Figure 1A:
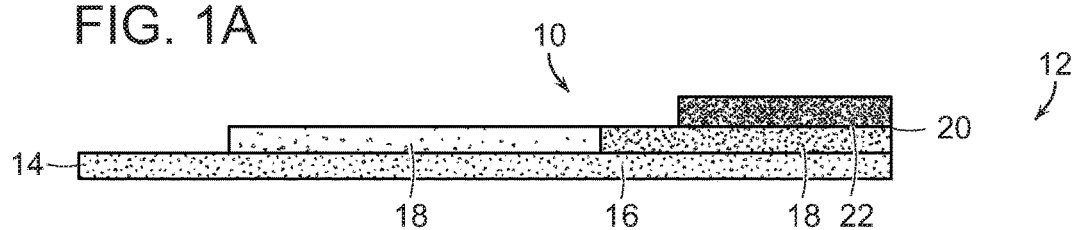
FIG. 1A is a side view of a test strip according to some embodiments of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The present disclosure is directed to systems and methods for measuring an analyte in a body fluid, such as, for example, glucose in blood. In some embodiments, the systems of the present disclosure may include a test strip on which a reaction between the analyte and suitable chemistry can take place and a meter in electrical communication with the test strip to measure an electrical signal generated by the reaction and to determine the concentration of the analyte. Each individual test strip may include a test strip control circuit programmed to have various information about the test strip, to control operation of the test strip, or both. The meter may be configured to communicate with the test strip control circuit upon insertion of the test strip into the meter.

FIG. 1A illustrates a general cross-sectional view of an embodiment of a test strip 10 consistent with the present invention. In some embodiments, the test strip of the present disclosure can be formed using materials and methods described in commonly owned U.S. Pat. No. 6,743,635 and U.S. patent application Ser. No. 11/181,778, which are hereby incorporated by reference in their entireties. In some embodiments, the test strip 10 may include a proximal connecting end 12, a distal end 14, and is formed with a base layer 16 extending along the entire length of test strip 10. Base layer or substrate 16 may be composed of an electrically insulating material and has a thickness sufficient to provide structural support to test strip 10. In some embodiments, the base layer 16 includes a electrically conductive layer covered with an electrically insulating material.

Figure 1B:
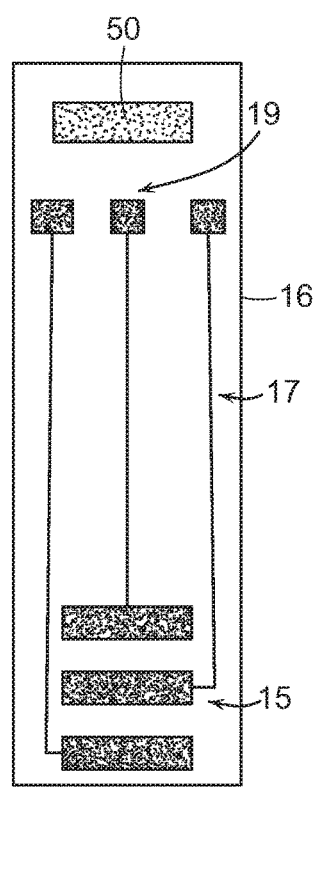
FIG. 1B is a top view of a conductive pattern on a substrate of a test strip according to some embodiments of the present disclosure.
Figure 5:
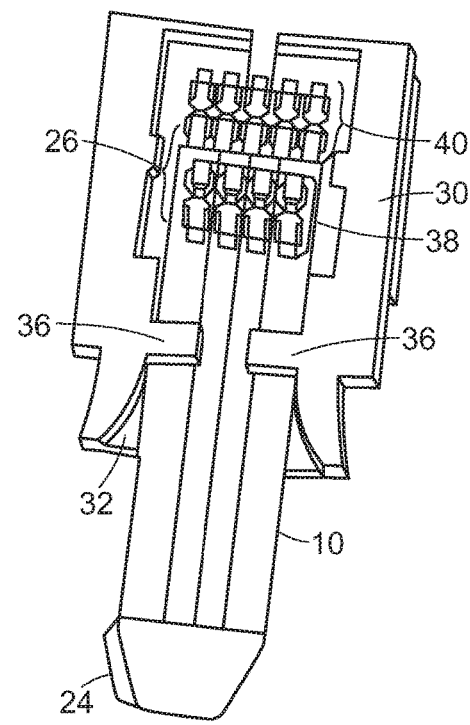
FIG. 5 shows a top view of a test strip inserted into a meter according to some embodiments of the present disclosure.

In reference to FIG. 1B, disposed on base layer 16 is a conductive pattern. In some embodiments, the conductive pattern may be formed by laser ablating the electrically insulating material of the base layer 16 to expose the electrically conductive material underneath. Other methods may also be used, such as inserted conductors with physical attachment to control circuit. Other methods may also be used to dispose the conductive pattern on the base layer. The conductive pattern may include a plurality of electrodes 15 disposed on base layer 16 near proximal end 12, a plurality of electrical strip contacts 19 disposed on base layer 16 near distal end 14, and a plurality of conductive traces 17 electrically connecting the electrodes 15 to the plurality of electrical strip contacts 19. As also seen in FIG. 5, the relative position of the measuring electrodes and the electrical strip contacts form a proximal electrode region 24 at one end of strip 10 and a distal strip contact region 26 at the other end. Referencing FIG. 1, in some embodiments, the plurality of electrodes may include a working electrode, a counter electrode, and fill-detect electrodes. In some embodiments, the conductive pattern may include multiple working electrodes for measuring different analytes or characteristics of the body fluid being tested.

A reagent layer may be disposed on the base layer 16 in contact with at least a working electrode of the conductive pattern. The reagent layer may include an enzyme, such as glucose oxidase, and a mediator, such as potassium ferricyanide or ruthenium hexamine. Reagent layer 90 may also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485). With these chemical constituents, reagent layer 90 reacts with glucose in the blood sample in the following way. The glucose oxidase initiates a reaction that oxidizes the glucose to gluconic acid and reduces the ferricyanide to ferrocyanide. When an appropriate voltage is applied to working electrode, relative to counter electrode, the ferrocyanide is oxidized to ferricyanide, thereby generating a current that is related to the glucose concentration in the blood sample.

Figure 1C:
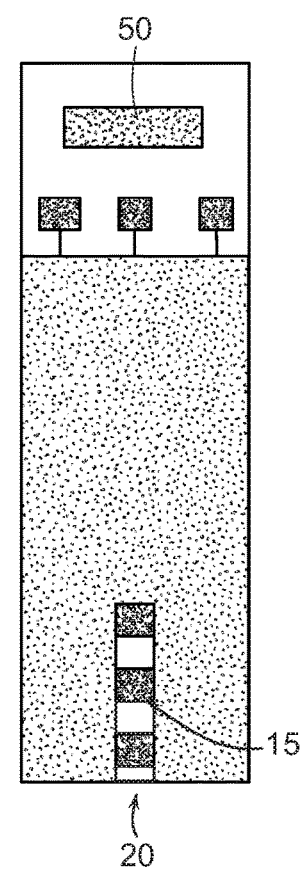
FIG. 1C is a top view of an assembled test strip according to some embodiments of the present disclosure.

As shown in FIG. 1B and FIG. 1C, a test strip controller 50 may be disposed near the distal end 14 of the test strip 10. In some embodiments, the test strip control circuit 50 may be positioned distally of the electrical strip contacts 19. The operation of the test strip control circuit is described in detail below.

Referring back to FIG. 1A, a dielectric insulating layer 18 may be formed over the conductive pattern along a portion of the test strip between the measuring electrodes and the plurality of electrical strip contacts in order to prevent scratching, and other damage, to the electrical connection. As seen in FIG. 1A, the proximal end 12 of test strip 10 may include a sample receiving location, such as a sample chamber 20 configured to receive a user's fluid sample. The sample chamber 20 may be formed in part through a slot formed between a cover 22 and the underlying measuring electrodes formed on base layer 16. The sample chamber has a first opening in the proximal end of the test strip and a second opening for venting the sample chamber. The sample chamber may be dimensioned so as to be able to draw the blood sample in through the first opening, and to hold the blood sample in the sample chamber, by capillary action. The test strip may include a tapered section that is narrowest at the proximal end, in order to make it easier for the user to locate the first opening and apply the blood sample. FIG. 1C illustrates a top view of a test strip of the present disclosure having a sample chamber 20 in which one or more electrodes 15 are disposed.

Figure 1D:
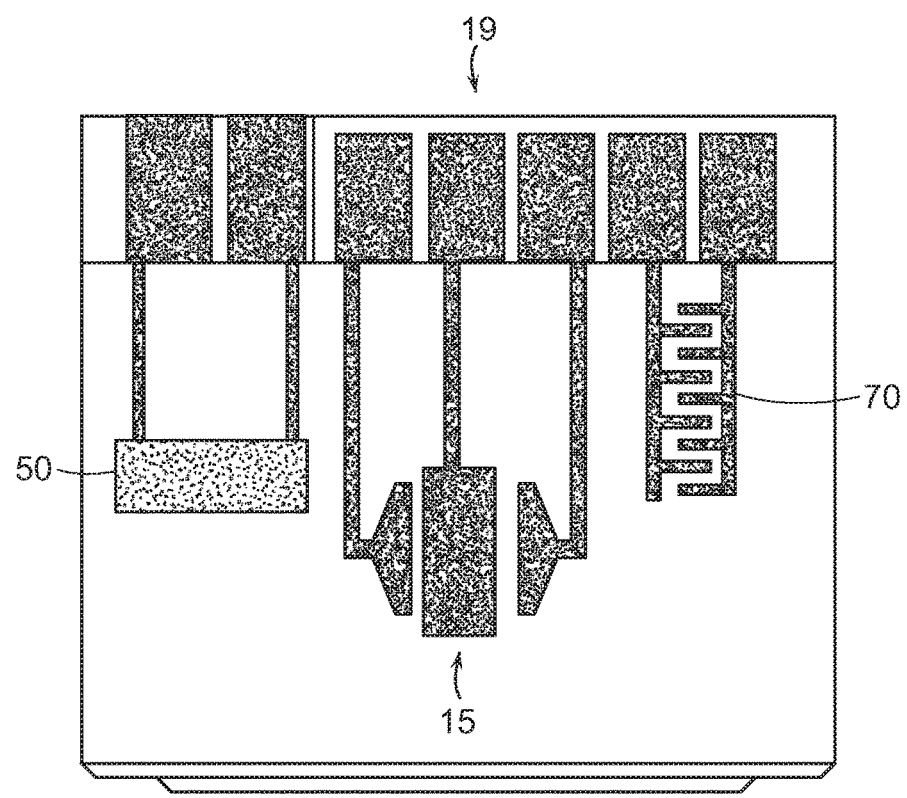
FIG. 1D is a top view of an embodiment of a conductive pattern on a substrate of a test strip with a separate humidity sensor according to some embodiments of the present disclosure.

In reference to FIG. 1D, in some embodiments, the distal region of the test strip 10 may include a plurality of electrical strip contacts 19. The electrical strip contacts 19 allow the meter to connect and communicate with the control circuit 50 and electrodes 15. In some embodiments, a humidity sensor 70 may be separately provided on the test strip 10. The humidity sensor 70 may also communicate with the meter through the electrical contacts 19. In some embodiments, the control circuit 50 may be located on the same substrate as the electrodes 15 and contacts 19 and humidity sensor 70. In some embodiments, the control circuit 50 may be provided separately from the substrate with the electrodes 15.

Figure 1E:
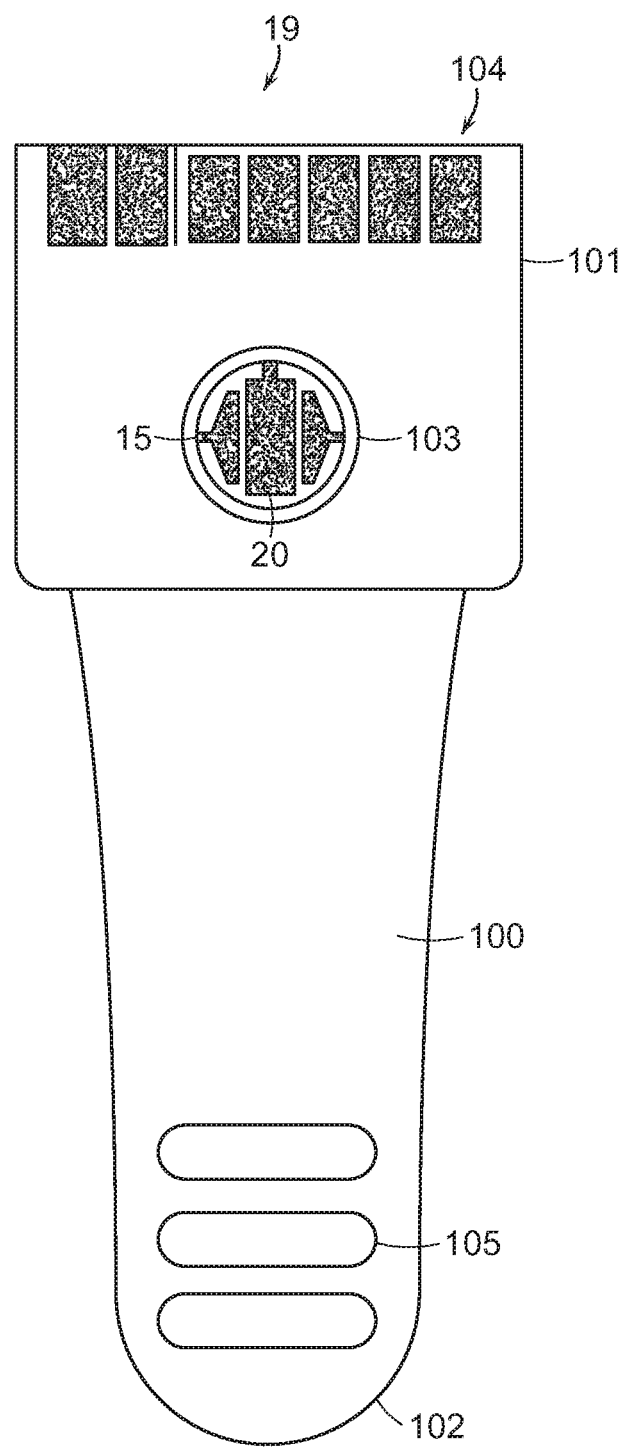
FIG. 1E is a top view of an embodiment of an assembled test strip contained within a plastic holder having a hand grip region according to some embodiments of the present disclosure.

In reference to FIG. 1E, in some embodiments, the test strip 10 may be encased by a carrier or shell 100. The shell 100 may have a distal end with a compartment or a chamber 101 configured to accept the test strip 100. In some embodiments, where the control circuit 50 is provided separately from the substrate with the electrode, the chamber 101 may be configured to accept the control circuit and the substrate separately. In some embodiments, the chamber 101 may have a window 103 exposing the electrodes 15 in the sample chamber 20. The chamber 101 may also include a cutout 104 exposing the contacts 19 to enable connection to the meter to allow for communication with the controller of the meter once the test strip 10 has been inserted into the meter. The shell 100 may be plastic or a polymer or any material that is comfortably gripped. The shell 100 has a proximal end 102 which may act as a handle to aid insertion of the test strip into the meter. The proximal end 102 may include raised ridges 105 to assist in gripping the shell 100. In some embodiments, the distal end 101 may be rectangular in shape, and in some embodiments has a width of about 10.5 mm and length of about 9 mm. A region between the distal end 101 and the proximal end 102 may gradually taper in width until terminating in a rounded proximal end 102. The shell 100 allows for the test strip 10 to be smaller and more affordably manufactured, while increasing the ease of use for a user.

Figure 2A:
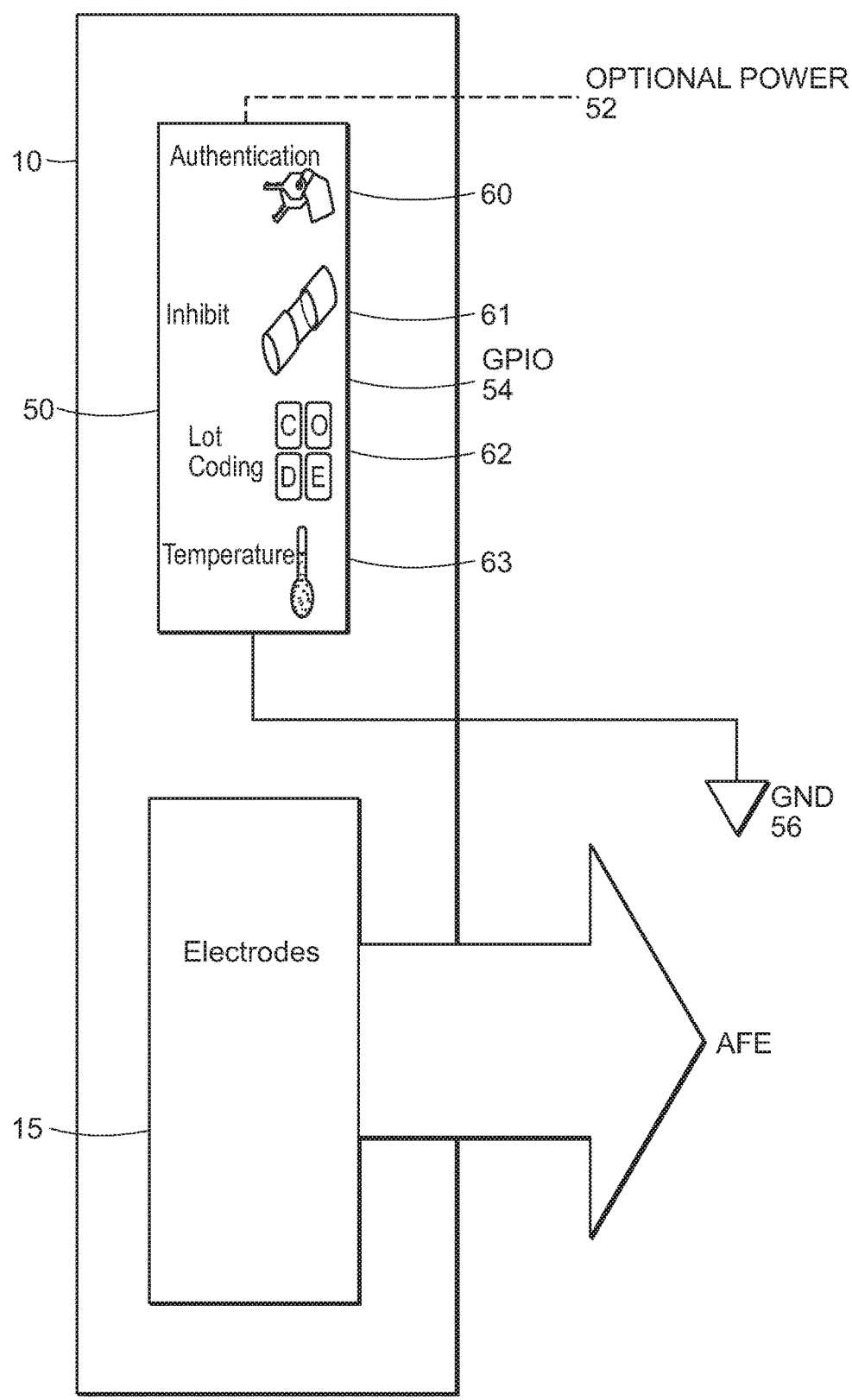
FIG. 2A and FIG. 2B illustrate a distal end of a test strip according to some embodiments of the present disclosure.

In reference to FIG. 2A, the control circuit 50 may be included directly on the test strip 10 in the distal end 14. In some embodiments, the control circuit 50 may be soldered in place or mounted with an anisotropic conductive film (ACF) or conductive epoxy or physical connector. Another possible mounting technique may involve connecting the control circuit to the test strip with conductive ink.

Figure 2B:
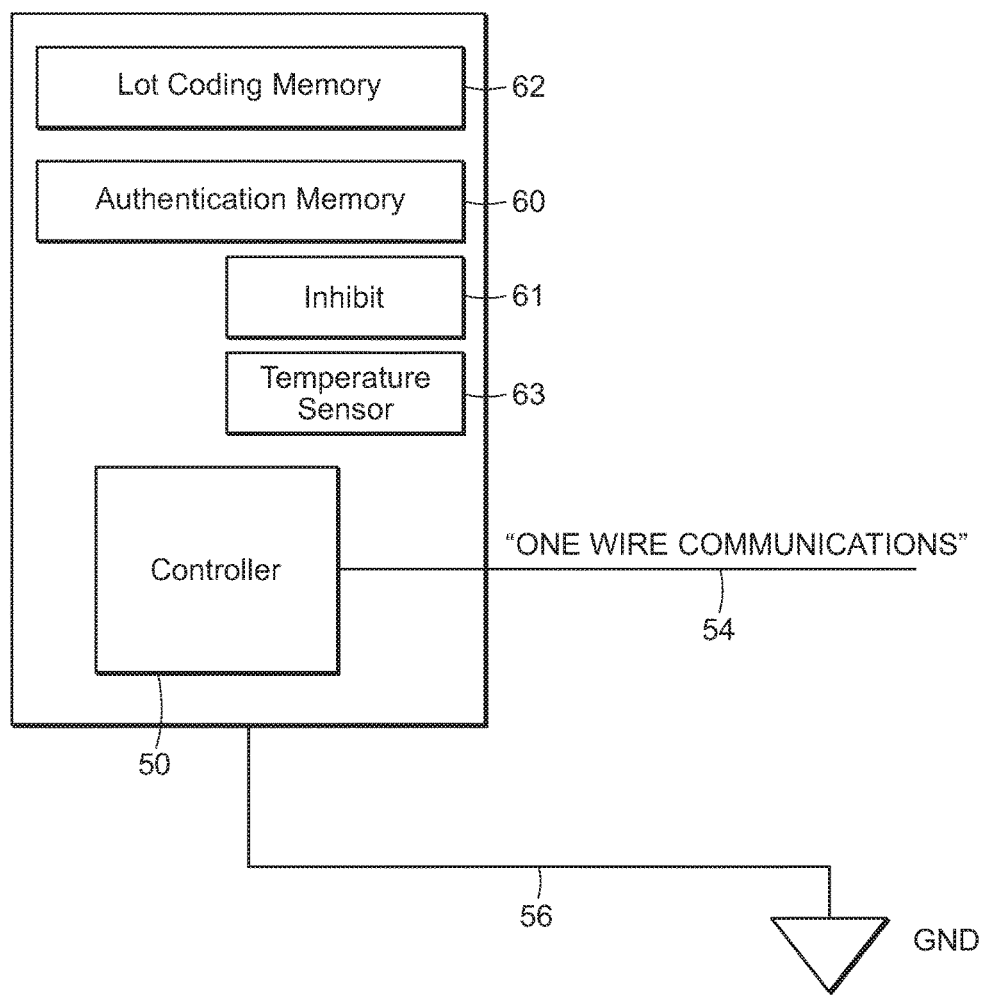

In reference to FIG. 2B, in some embodiments, the control circuit may include an integrated circuit (IC) with a "one wire" interface (ground is also required) 54. The IC may include an embedded temperature sensor 63, and separate memories/logic for lot coding 62, data storage and authentication 60. In addition, an inhibit logic 61 can be one time programmable (OTP) memory or a digital fuse. These peripherals may be controlled by a controller 50 which interfaces to the meter on the "one wire" interface 54.

The controller may have a "one-wire" digital interface 54, which requires only one data signal to communicate with the control circuit 50. A grounding wire 56 may be provided to connect the control circuit 50 to the ground connector of the meter (not pictured) to extract information from the control circuit 50, and to inhibit a security fuse of the test strip. A "one wire" interface 54 is a common way to communicate with ICs where connector pins are limited or GPIO (General Purpose Input/Output) lines on a processor are limited. A single GPIO can communicate via the "one wire" interface using the required protocol identified in the IC datasheet.

The control circuit 50 may have an optional power source 52 and a generic pin 54 acting as a general-purpose input/output (GPIO). In some embodiments, the IC is designed to self power from the energy of the "one wire" interface 54. Alternatively or additionally, an optional power source 52 may be provided in some IC design. A GPIO from the meter could power the IC with a logic 1 for ON and a logic 0 for OFF.

In one embodiment, the control circuit 50 is comprised of a very small integrated circuit (IC), approximately 2 mm×2 mm, with a low profile height. The small size of the IC allows for integration into blood glucose monitor strips which are typically 5-9 mm wide×17-28 mm long and very low profile (<1 mm). In one embodiment, the IC is embedded within the strip layers so there is no additional thickness of the strip. Another embodiment places the IC on the surface of the strip as in an SMT (surface mount technology) component.

The control circuit 50 may be programmed for test strip recognition and control. The control circuit 50 can be programmed at the time of manufacturing for the autocode and authentication using factory programming equipment on the strip line. Alternately, the ICs may be preprogrammed at the factory making the ICs.

The incorporation of individualized code data within individual test strips provides numerous advantages. For example, a user no longer needs to manually enter the meter's lot code, eliminating the possibility of user error. In some embodiments, the control circuit may include autocode data related to the test strip, which may allow the meter's microprocessor to access and utilize a specific set of stored calibration values. The memory could be implemented as a non-volatile string of 8-96 bits. This approach may significantly increase the number of autocodes. For a digital (binary) code, the number of autocodes is $2^n-1$, where n is the number of bits. The "−1" is to subtract out the case where all bits are on, which looks identical to "no strip inserted" and would not trigger the system. In some embodiments, the control circuit may be provided with 8 bits, resulting in 258 unique autocode combinations. In some embodiments, the control circuit 50 may include calibration values related to the test strip that the control circuit can communicate to the meter. In some embodiments, the control circuit may have writable memory where the test strip glucose value or an error code could be stored for that used strip. In the case where data is stored on the strip, that strip may be read by another external device to extract the glucose value or error message stored on the strip.

Figure 2C:
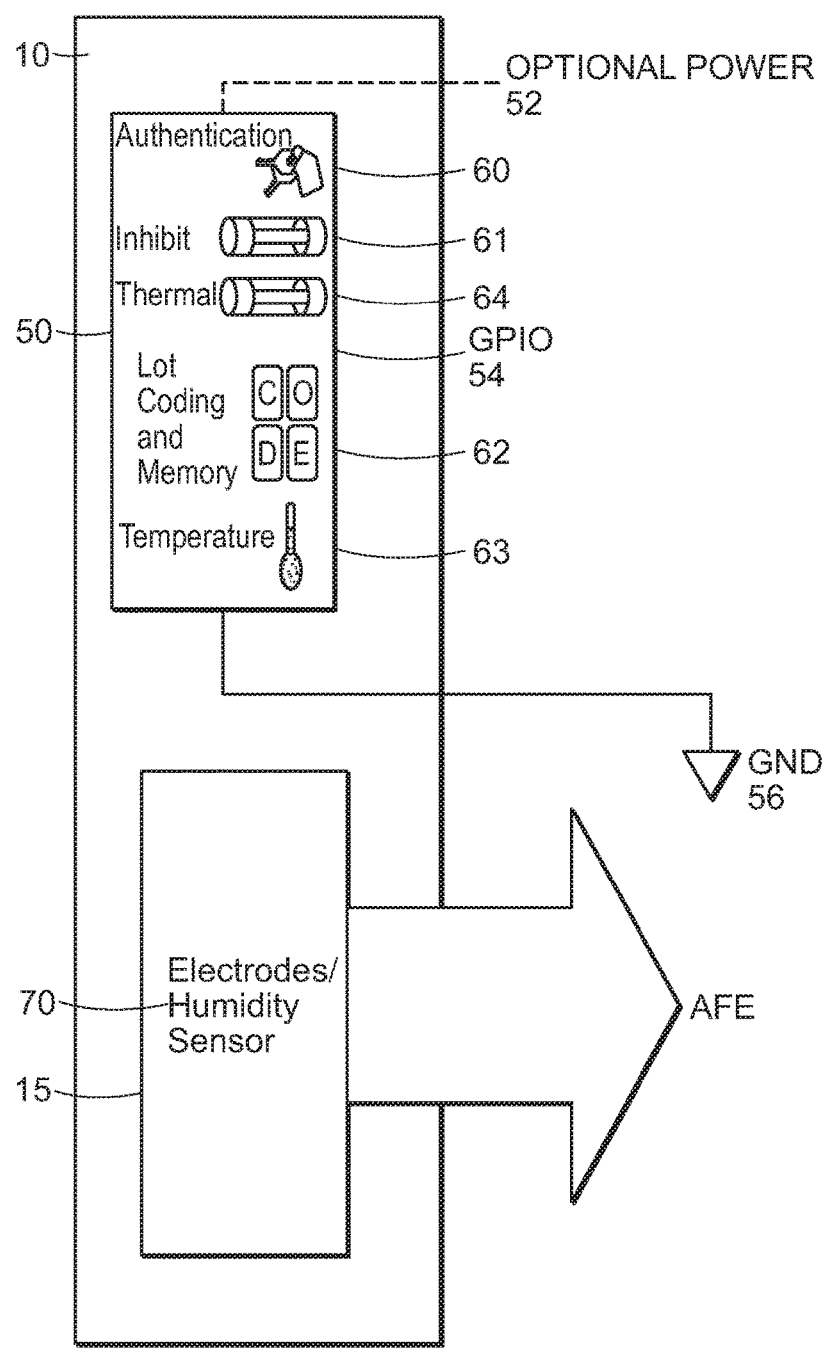
FIG. 2C and FIG. 2D illustrate a distal end of a test strip with a humidity or thermal sensor according to some embodiments of the present disclosure.
Figure 2D:
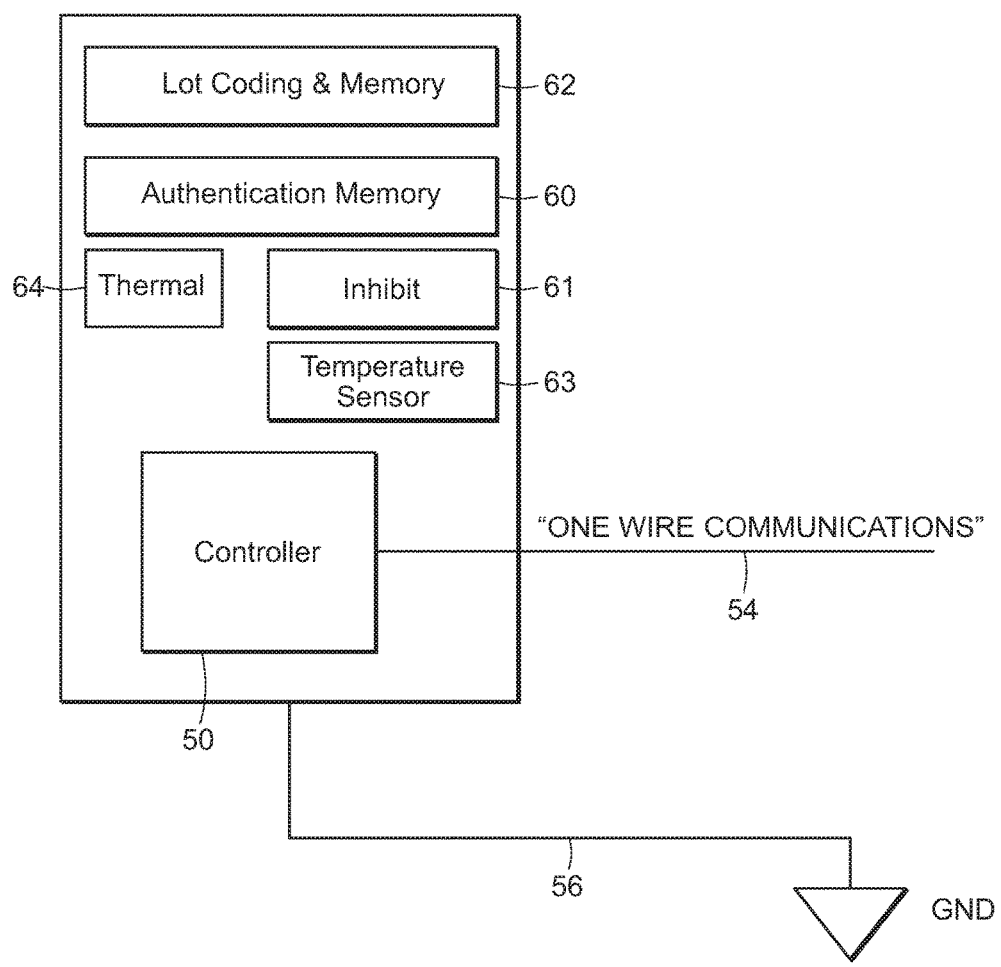

Referring now to FIGS. 2C and 2D, in some embodiments, the control circuit 50 may be programmed to monitor the temperature of the test strip. The control circuit 50 may monitor the surrounding temperature and convert the analog signal to a digital number for transmission over the one-wire interface 54. In some embodiments, the control circuit 50 may be programmed with temperature limits 63 that are important to maintain for proper performance of the test strip. For example, testing glucose with a test strip that is too hot or too cold may return an inaccurate result. If a programmed temperature limit is exceeded, a thermal fuse 64 on the control circuit may be blown to prevent future use of the strip at a temperature outside selected temperature range. Test strips with a blown thermal fuse in the control circuit 50 can be rejected by the meter to prevent use of the test strip 12. This can ensure that users do not use a test strip 12 that may have been compromised due to exposure to temperature extremes. In some embodiments, the control circuit 50 may be programmed to monitor other environmental factors, such as humidity, pressure, etc., in addition to or instead of temperature. Similar to temperature limits, the controller may be programmed with limits for environmental factors and may be deactivated as described above upon exposer to environmental conditions outside programmed ranges. Aside from the control circuit 50, the strip 12 may contain components, such as thermal fuses that can operate without the device present, to disable the strip in the event that it encounters a temperature or humidity outside the acceptable range. In some embodiments, the humidity sensor 70 may reside outside the control circuit for better environmental exposure.

In some embodiments, the control circuit may include a non-volatile digit strings (48 for example) which may serve as a unique password to authenticate the test strip as valid prior to taking a measurement. This can ensure that a user is using an approved strip.

In some embodiments, the control circuit 50 may be programmed to inhibit or lock the test strip after use to prevent re-use of the test strip by the user. In some embodiments, after the measurements are complete, a fuse on the control circuit may be blown. Because the fuse cannot be reset, the meter can reject the test strips with a blown fuse in the control circuit to prevent re-use of the test strips. In some embodiments, after the test is complete, the meter may send a high voltage/high current pulse to physically overload a circuit element in the control circuit. In some embodiments, a low voltage/current signal of sufficient time may be delivered to the control circuit so as to raise the energy state of a semiconductor memory cell(s) such that the higher energy state inhibits read/writes to the control circuit. In some embodiments, a bit is dedicated as a check which is set after a single use.

Figure 3:
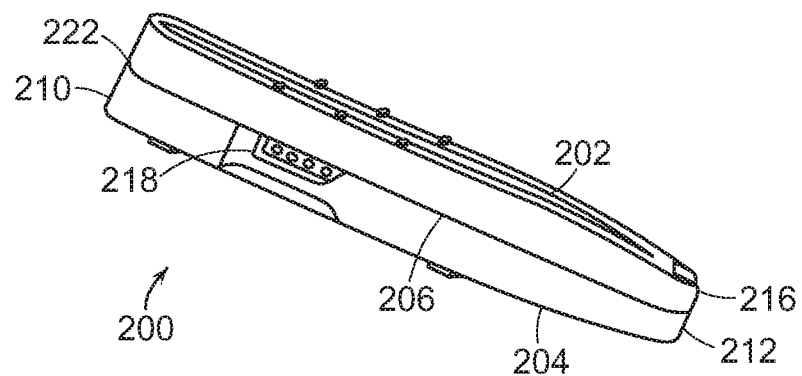
FIG. 3 and FIG. 4 illustrate a meter according to certain embodiments of the present disclosure.
Figure 4:
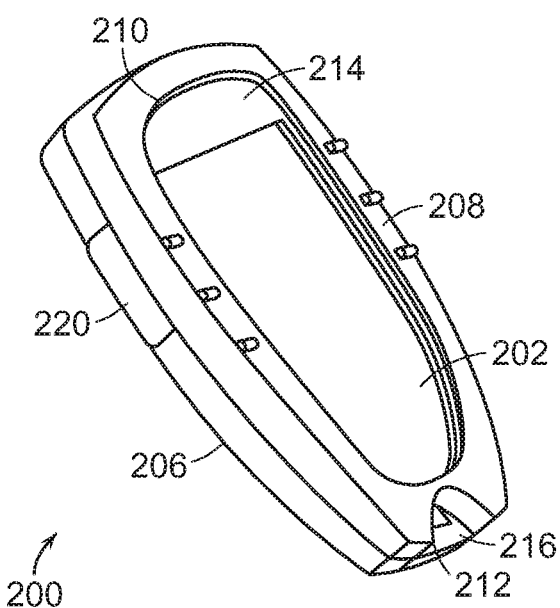

To measure the glucose level in a blood sample, test strip 10 is preferably used with a meter, as shown in FIG. 3 and FIG. 4. Preferably, meter 200 has a size and shape to allow it to be conveniently held in a user's hand while the user is performing the glucose measurement. Meter 200 may include a front side 202, a back side 204, a left side 206, a right side 208, a top side 210, and a bottom side 212. Front side 202 may include a display 214, such as a liquid crystal display (LCD). Bottom side 212 may include a strip connector 216 into which test strip 10 is inserted to conduct a measurement.

Left side 206 of meter 200 may include a data connector 218 into which a removable data storage device 220 may be inserted, as necessary. Top side 210 may include one or more user controls 222, such as buttons, with which the user may control meter 200, and the right side 208 may include a serial connector (not shown).

FIG. 5 illustrates a top perspective view of a test strip 10 inserted within a meter connector 30 consistent with the present invention. Test strip 10 includes a proximal electrode region 24, which contains the sample chamber and measuring electrodes, as described above. Proximal electrode region 24 may be formed to have a particular shape in order to distinguish to the user the end receiving a fluid sample from distal strip contact region 26. Meter connector 30 includes channel 32 extending out to a flared opening for receiving the test strip 10. Meter connector 30 may further include tangs 36 extending a predetermined height above the base of channel 32. The predetermined height of tangs 36 is selected to limit the extent, such as through a corresponding raised layer of test strip 10, to which a test strip 10 can be inserted into channel 32. Meter connector 30 may include a first plurality of connector contacts 38, disposed closer to the proximal end of meter connector 30, which are configured to contact the electrical strip contacts 19 upon insertion of the test strip 10 into the meter connector 30. In some embodiments, the test strip control circuit reader 40 may be disposed closer to the distal end of meter connector 30 to communicate with the test strip control circuit 50. In some embodiments, the meter may be provided with one or more GPIO lines for communication with the IC. The one or more GPIO lines may replace digital coding lines (typically 3-5) utilizing GPIOs.

Figure 6:
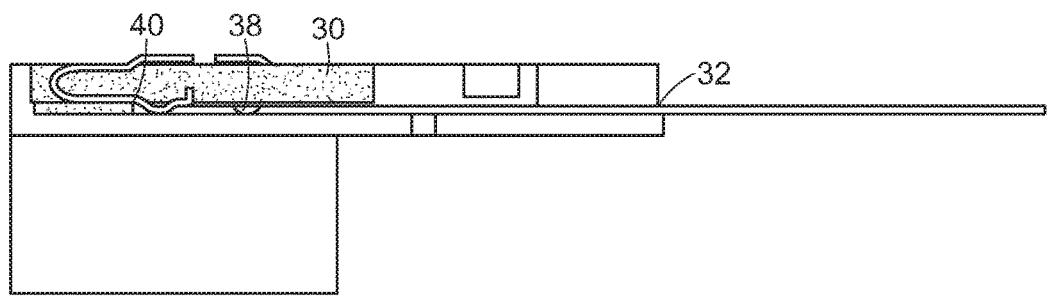
FIG. 6 is a side view of a test strip inserted into a meter according to some embodiments of the present disclosure.

FIG. 6 illustrates a general cross-sectional view of a test strip inserted within meter connector 30 consistent with the present invention. Channel 32 depicts a proximal row of connectors comprising a plurality of connector contacts 38 for connection the electrical strip contacts 19 upon insertion of the test strip 10 into the meter connector 30.

Figure 7A:
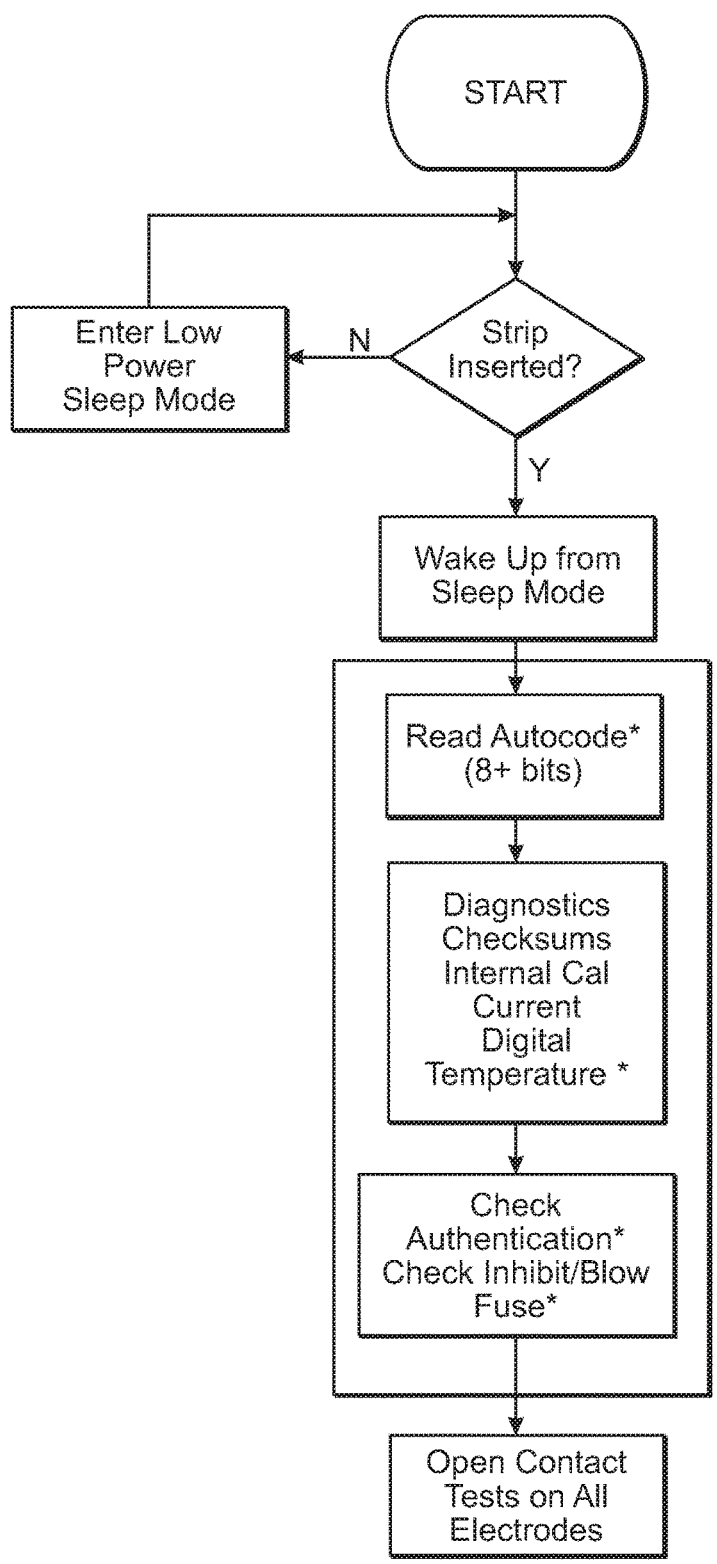
FIG. 7A and FIG. 7B present a flow chart showing a test routine according to some embodiments of the present disclosure.
Figure 7B:
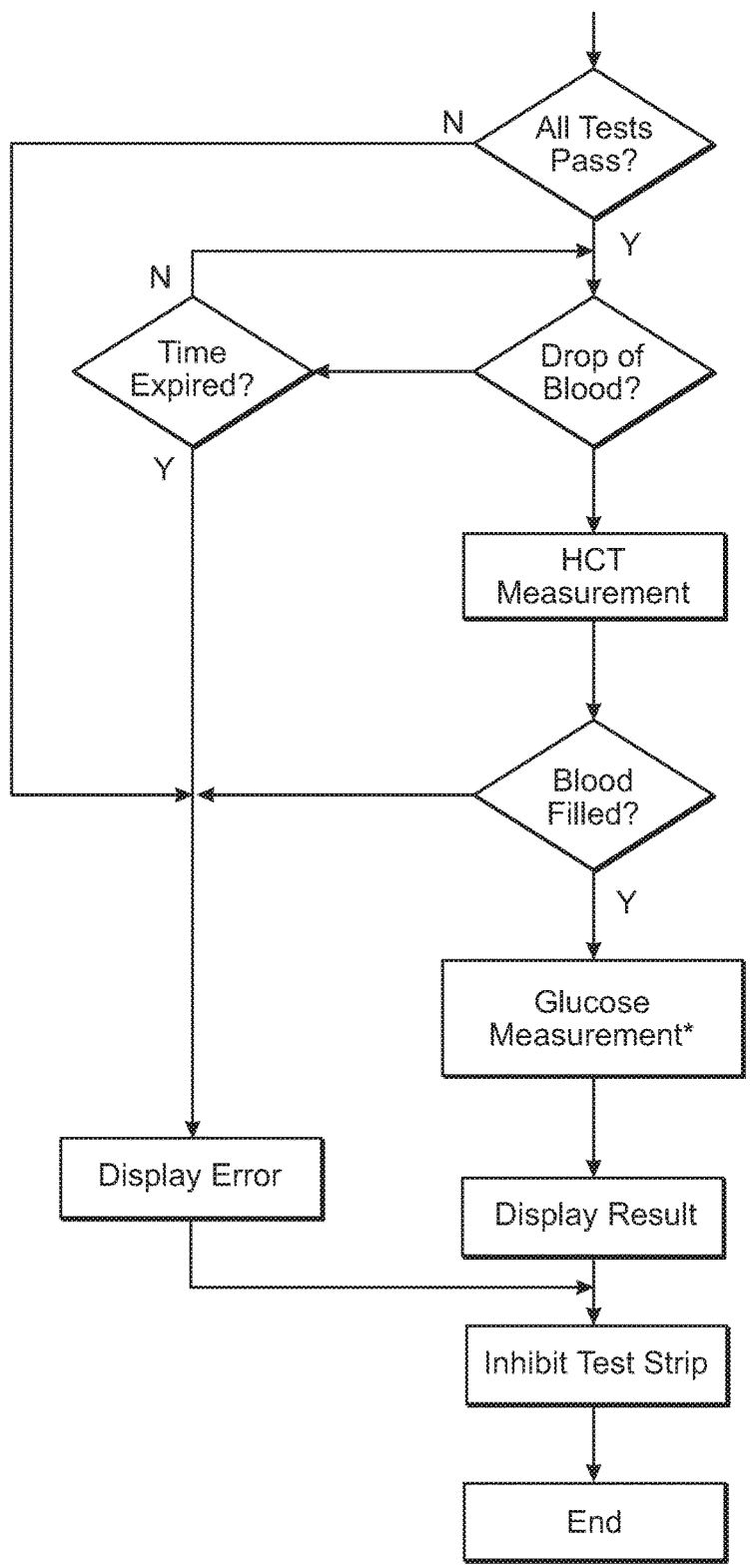

In reference to FIG. 7A and FIG. 7B, the meter may be battery powered and may stay in a low-power sleep mode when not in use in order to save power. When the test strip is inserted into the meter, current flow to the meter causes the meter to wake up and enter an active mode. Alternatively, the meter may be provided with a wake button.

Next, the meter can connect to the control circuit to read the code information from the control circuit and can then identify, for example, the particular test to be performed, or a confirmation of proper operating status. In addition, the meter can also identify the inserted strip as either a test strip or a check strip based on the particular code information. If the meter detects a check strip, it performs a check strip sequence. If the meter detects a test strip, it performs a test strip sequence.

In addition, the meter can ensure that the test strip is authentic and has not been previously used. The meter will also read the temperature of the test strip. Diagnostics may include checksums or cyclic redundancy checks (CRC) of portions of the internal and/or external memory to establish confidence that the memory is not corrupted because the checksum/crc data calculated matches the programmed checksum/crc. Another diagnostics test that may be performed is an LCD test to verify the integrity of the LCD to gain confidence it is not cracked and will display the proper result to the user that is sent to it. Another diagnostic test that may be performed is an internal calibration current test to verify that the analog front end continues to measure an accurate current within the margin of error allowed.

If all information checks out, the meter can perform open contact tests on all electrodes to validate the electrodes. The meter may validate the electrodes by confirming that there are no low-impedance paths between any of these electrodes. If the electrodes are valid, the meter indicates to the user that sample may be applied to the test strip and the meter can perform analyte measurements.

In some embodiments, the systems of the present disclosure may be used to measure glucose concentration in blood. Once the meter has performed an initial check routine, as described above, the meter may apply a drop-detect voltage between a working and counter electrodes and detect a fluid sample, for example, a blood sample, by detecting a current flow between the working and counter electrodes (i.e., a current flow through the blood sample as it bridges the working and counter electrodes). For example, in some embodiments, the meter may measure an amount of components in blood which may interfere with the glucose measurement, such as, for example, a level of hematocrit. The meter may later use such information to adjust the glucose concentration to account for the presence of the interferants in blood.

Next, to detect that an adequate sample is present in the sample chamber and that the blood sample has traversed the reagent layer and mixed with the chemical constituents in the reagent layer, the meter may apply a fill-detect voltage between the fill-detect electrodes and measure any resulting current flowing between the fill-detect electrodes. If this resulting current reaches a sufficient level within a predetermined period of time, the meter indicates to the user that adequate sample is present and has mixed with the reagent layer.

In one embodiment, the test strip meter comprises a decoder for decoding a predetermined electrical property, e.g. resistance, from the test strips as information. The decoder operates with, or is a part of, a microprocessor.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample.

In one example, the reagent layer may react with glucose in the blood sample in order to determine the particular glucose concentration. In one example, glucose oxidase is used in the reagent layer. The recitation of glucose oxidase is intended as an example only and other materials can be used without departing from the scope of the invention. Other possible mediators include, but are not limited to, ruthenium and osmium. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user.

It should be noted that while the operation of the system of the present disclosure has been described primarily in connection with determining glucose concentration in blood, the systems of the present disclosure may be configured to measure other analytes in blood as well as in other fluids.

Once all the tests are completed, the meter may inhibit the test strip as described above to prevent re-use of the test strip.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A system for measuring a property of a sample in a liquid, comprising:
   a diagnostic test strip for collecting a sample, the strip having a plurality of electrodes for measuring a property of the sample, and the strip having a control circuit at a distal region of the strip, configured to communicate with a controller of a meter, the control circuit including an embedded temperature sensor, a memory for lot coding and authentication of the test strip, and an inhibit logic for inhibiting the test strip from being used after removal of the test strip from the meter; and
   a diagnostic meter for receiving the test strip, the meter having a controller programmed to communicate with the control circuit.

2. The system according to claim 1, wherein the control circuit comprises a non-volatile string of bits used to identify the strip as authentic.

3. The system according to claim 1, wherein the control circuit comprises a non-volatile string of bits used as lot codes.

4. The system according to claim 1, wherein the controller of the meter is further programmed to perform a test utilizing the test strip and to inhibit the test strip after the test has been completed.

5. The system according to claim 1, wherein the control circuit is configured to measure a temperature of the test strip, wherein the control circuit is programmed to communicate to the controller to adjust a test measurement based on the temperature of the test strip.

6. The system of claim 5, wherein the control circuit is programed to inhibit the test strip when the temperature is outside a pre-selected range of temperatures.

7. The system according to claim 1, wherein the control circuit is configured to store a glucose value measured during the test.

8. The system according to claim 1, wherein the control circuit is configured to store an error message generated during the test.

9. The system according to claim 1, wherein the control circuit is configured to measure a humidity of the test strip.

10. The system of claim 1, wherein the inhibit logic includes a fuse configured to be blown upon measurement of the property of the sample.

11. A system for measuring a property of a sample, comprising:
    a diagnostic test strip for collecting a sample, the strip having a plurality of electrodes for measuring a property of the sample, and the strip having an embedded humidity sensor, and a control circuit at a distal region of the strip, configured to communicate with a controller of a meter, the control circuit including an embedded temperature sensor, a memory for lot coding and authentication of the test strip, and an inhibit logic for inhibiting the test strip from being used after removal of the test strip from the meter, wherein the inhibit logic includes a fuse; and
    a diagnostic meter for receiving the test strip, the meter having a controller programmed to communicate with the humidity circuit and with the control circuit.

12. The system of claim 11, wherein the humidity sensor is configured to measure a humidity of the test strip and communicate the humidity to the controller, wherein the controller is programmed to adjust a test measurement based on the humidity of the test strip.

13. A diagnostic test strip comprising:
    an electrically insulating layer;
    a conductive pattern formed on the insulating layer including a plurality of electrodes for measuring a property of a sample and disposed on the insulating layer at a proximal region of the strip;
    electrical strip contacts disposed on the insulating layer at a distal region of the strip, and conductive traces electrically connecting the electrodes to at least some of the electrical strip contacts;
    a reagent layer contacting at least a portion of at least one electrode; and
    a control circuit disposed at the distal region of the strip, connected to the electrodes and configured to communicate with a controller of a meter, the control circuit including an embedded temperature sensor, a memory for lot coding and authentication of the test strip, and an inhibit logic for inhibiting the test strip from being used after removal of the test strip from the meter, wherein the inhibit logic includes a fuse.

14. The test strip of claim 13, wherein the control circuit comprises a non-volatile string of bits used to identify the strip as authentic.

15. The test strip of claim 13, wherein the control circuit comprises a non-volatile string of bits used as lot codes.

16. The test strip of claim 13, wherein the control circuit is configured to measure a temperature of the test strip, wherein the control circuit is programmed to communicate to the controller to adjust a test measurement based on the temperature of the test strip.

17. The test strip of claim 13, wherein the control circuit is configured to store a glucose value measured during the test.

18. The test strip of claim 13, wherein the control circuit is configured to store an error message generated during the test.

19. The test strip of claim 13, wherein the control circuit is configured to measure a humidity of the test strip, wherein the control circuit is programmed to communicate to the controller to adjust a test measurement based on the humidity of the test strip.

20. The test strip of claim 13, wherein the control circuit is programed to inhibit the test strip when the temperature is outside a pre-selected range of temperatures.

21. The test strip of claim 13, further comprising a shell configured to accept the test strip, the shell having:
 a chamber at a distal end, the chamber being configured to accept the test strip and having a first window exposing the electrodes and a second window exposing the contacts to enable connection to the meter to allow for communication with the controller of the meter once the test strip has been inserted into the meter; and
 a handle at a proximal end to aid insertion of the test strip into the meter.

22. A method for measuring a concentration of glucose in a blood sample comprising:
 providing a diagnostic test strip for collecting a blood sample, the strip having a plurality of electrodes for measuring a property of the sample, and the strip having a control circuit at a distal region of the strip, configured to communicate with a controller of a meter, the control circuit including an embedded temperature sensor, a memory for lot coding and authentication of the test strip, and an inhibit logic for inhibiting the test strip from being used after removal of the test strip from the meter, wherein the inhibit logic includes a fuse;
 providing a meter for receiving the test strip, the meter having a controller programmed to communicate with the control circuit;
  inserting the test strip into the meter to enable communication between the controller and the control circuit;
  causing the control circuit to run diagnostics on the test strip, the diagnostics being one or more of reading autocode information, identifying the test strip, authenticating the test strip, calibrating the analog front end of the test strip, measuring a temperature of the test strip, and validating any electrodes on the test strip;
  applying a blood sample to the test strip;
  measuring a resistance of the blood sample and using the resistance to determine the glucose concentration in the blood sample; and
  causing the control circuit to inhibit the test strip from being used again.

23. A system for measuring a property of a sample in a liquid, comprising:
 a diagnostic test strip for collecting a sample, the strip having a plurality of electrodes for measuring a property of the sample, and the strip having a control circuit at a distal region of the strip, configured to communicate with a controller of a meter, the control circuit including an embedded temperature sensor, a memory for lot coding and authentication of the test strip, and an inhibit logic for inhibiting the test strip from being used more than once; and
 a diagnostic meter for receiving the test strip, the meter having a controller programmed to communicate with the control circuit,
 wherein the control circuit is configured to measure a temperature of the test strip, wherein the control circuit is programed to inhibit the test strip when the temperature is outside a pre-selected range of temperatures, and wherein the control circuit includes a thermal fuse.

* * * * *